US010925679B2

(12) United States Patent
Hahn et al.

(10) Patent No.: US 10,925,679 B2
(45) Date of Patent: Feb. 23, 2021

(54) POSITION DETERMINATION DEVICE FOR DETERMINING A POSITION OF AN INSTRUMENT WITHIN A TUBULAR STRUCTURE

(71) Applicant: Fraunhofer-Gesellschaft zur Foerderung der angewandten Forschung e.V., Munich (DE)

(72) Inventors: Horst Hahn, Bremen (DE); Torben Pätz, Bremen (DE)

(73) Assignee: Fraunhofer-Gesellschaft zur Foerderung der angewandten Forschung e.V., Munich (DE)

( * ) Notice: Subject to any disclaimer, the term of this patent is extended or adjusted under 35 U.S.C. 154(b) by 65 days.

(21) Appl. No.: 16/341,810

(22) PCT Filed: Oct. 12, 2017

(86) PCT No.: PCT/EP2017/076101
§ 371 (c)(1),
(2) Date: Apr. 12, 2019

(87) PCT Pub. No.: WO2018/069462
PCT Pub. Date: Apr. 19, 2018

(65) Prior Publication Data
US 2019/0314090 A1 Oct. 17, 2019

(30) Foreign Application Priority Data

Oct. 13, 2016 (DE) .................. 10 2016 119 579.0

(51) Int. Cl.
*A61B 34/20* (2016.01)
*G06T 7/64* (2017.01)
*A61B 34/10* (2016.01)

(52) U.S. Cl.
CPC ............. *A61B 34/20* (2016.02); *G06T 7/64* (2017.01); *A61B 2034/105* (2016.02); *A61B 2034/2061* (2016.02)

(58) Field of Classification Search
CPC ............. A61B 34/20; A61B 2034/105; A61B 2034/2061; G06T 7/64
See application file for complete search history.

(56) References Cited

U.S. PATENT DOCUMENTS

2014/0336501 A1* 11/2014 Masumoto ......... A61B 1/00055
                                                              600/417
2015/0254526 A1    9/2015 Denissen
2016/0302869 A1* 10/2016 Chopra ............... A61B 5/066

FOREIGN PATENT DOCUMENTS

DE   10 2016 119 579    4/2018
JP        2016-502412   1/2016
(Continued)

OTHER PUBLICATIONS

International Search Report (with translation) and Written Opinion of the International Searching Authority completed Jun. 27, 2019, in International Patent Application No. PCT/EP2019/059266, 13 pages.

(Continued)

*Primary Examiner* — Casey L Kretzer
(74) *Attorney, Agent, or Firm* — Ellen M. Bierman; Lowe Graham Jones PLLC

(57) ABSTRACT

Methods, systems, and techniques are provided to a position determination device for determining a position of an instrument within a tubular structure. The position determination device comprises a first curvature values providing unit for providing first curvature values being indicative of first curvatures of the tubular structure at several first locations along the tubular structure and a second curvature values providing unit for providing second curvature values being indicative of second curvatures of the instrument at several (Continued)

second locations along the instrument. A position determination unit determines the position of the instrument within the tubular structure based on the first and second curvature values.

19 Claims, 6 Drawing Sheets

(56) References Cited

FOREIGN PATENT DOCUMENTS

| JP | 2016-508399 | 3/2016 | |
|---|---|---|---|
| WO | 2005/084571 | 9/2005 | |
| WO | 2014/028400 | 2/2014 | |
| WO | 2014/053925 | 4/2014 | |
| WO | 2014/191262 | 12/2014 | |
| WO | WO-2015089013 A1 * | 6/2015 | ............ A61B 1/267 |
| WO | 2018/069462 | 4/2018 | |

OTHER PUBLICATIONS

International Search Report and Written Opinion of the International Searching Authority completed Dec. 8, 2017, in International Patent Application No. PCT/EP2017/076101, 11 pages.

* cited by examiner

POSITION DETERMINATION DEVICE FOR DETERMINING A POSITION OF AN INSTRUMENT WITHIN A TUBULAR STRUCTURE

CROSS-REFERENCE TO RELATED APPLICATIONS

This application is a U.S. national phase of International Patent Application No. PCT/EP2017/076101, filed Oct. 12, 2017; which claims priority from Germany Patent Application No. 102016119579.0, filed Oct. 13, 2016, the contents of which applications are incorporated herein by reference in their entireties.

TECHNICAL FIELD

The disclosure relates to a position determination device, method and computer program for determining a position of an instrument like a catheter within a tubular structure. The disclosure relates further to an imaging system comprising the position determination device, and an imaging method and imaging computer program.

BACKGROUND

In medical applications position determination devices are known which use electromagnetic (EM) or optical shape sensing (OSS) tracking techniques for determining a position of an interventional instrument within a patient's body. However, the EM and OSS tracking techniques can be relatively inaccurate due to, for instance, EM field inhomogeneities and errors in interpolating and integrating curvature information, respectively.

SUMMARY

The present disclosure describes a position determination device, method and computer program which allow for an improved determination of a position of an instrument within a tubular structure. Further, it describes an imaging system comprising the position determination device, and an imaging method and an imaging computer program.

DETAILED DESCRIPTION

Figure 1:
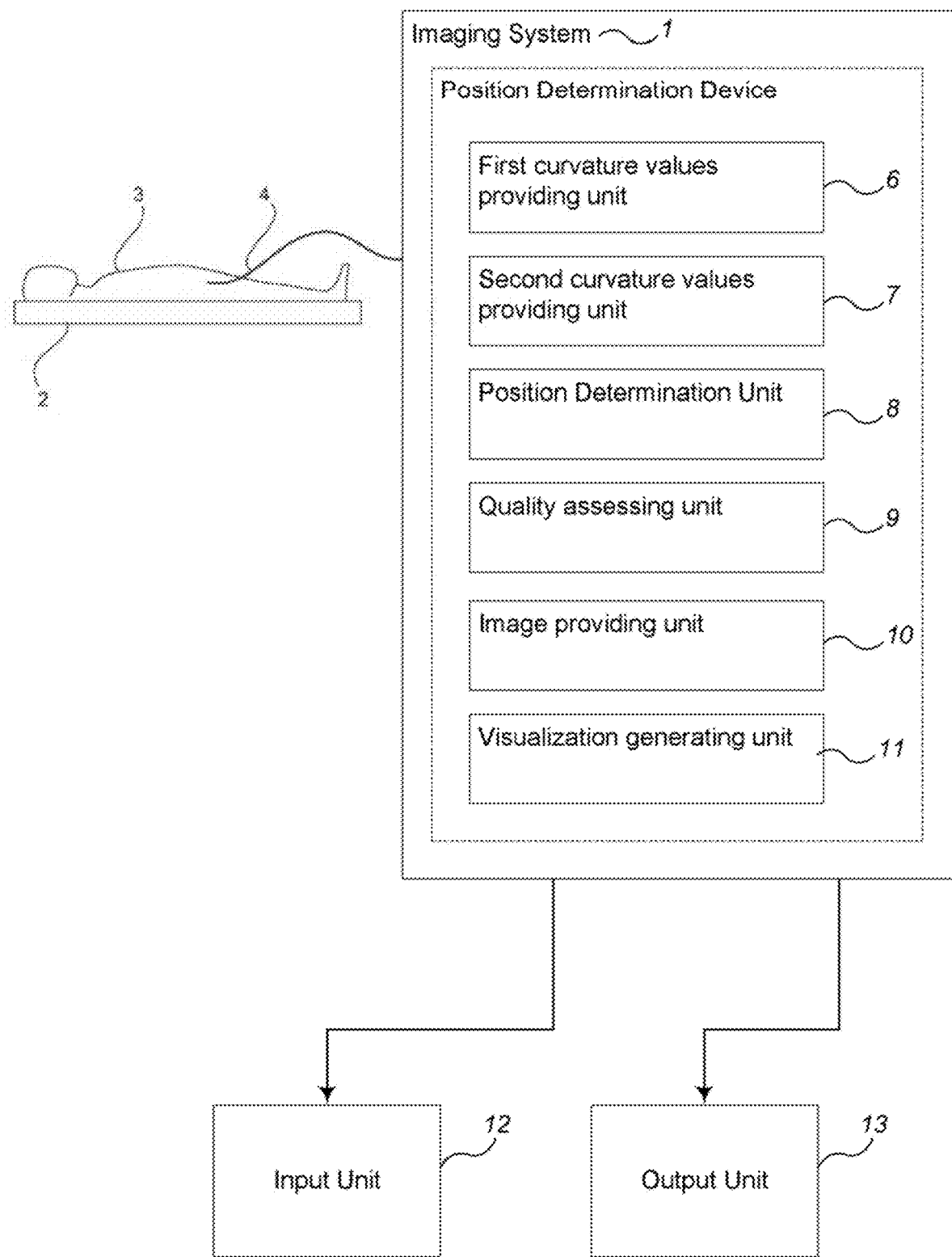
FIG. 1 shows schematically and exemplarily an embodiment of an imaging system.

The present disclosure describes a position determination device, method and computer program which allow for an improved determination of a position of an instrument within a tubular structure. Further, it describes an imaging system comprising the position determination device, and an imaging method and an imaging computer program.

In a first aspect, a position determination device for determining a position of an instrument within a tubular structure is presented, wherein the position determination device comprises:

a first curvature values providing unit for providing first curvature values being indicative of first curvatures of the tubular structure at several first locations along the tubular structure, a second curvature values providing unit for providing second curvature values being indicative of second curvatures of the instrument at several second locations along the instrument, a position determination unit for determining the position of the instrument within the tubular structure based on the first and second curvature values.

The first curvatures at the several first locations along the tubular structure and the second curvatures at the several second locations along the instrument are local curvatures. By determining the position of the instrument within the tubular structure based on this local information and not based on global information the accuracy of determining the position can be significantly improved, because it is less sensitive to measurement errors. For instance, the accuracy of determining the position can be less sensitive, in particular, not sensitive at all, to global measurement errors like drift, field inhomogeneities, et cetera. Moreover, the position determination unit can be adapted to determine the position of the instrument without, for instance, the need of reconstructing the shape of the instrument. Thus, a set of local first curvature values and a set of local second curvature values, i.e. the first and second curvature values, can be used for determining the position of the instrument relative to the tubular structure, without requiring a reconstruction of the shape of the instrument based on the second curvature values.

The position determination unit is preferentially adapted to determine the location of the instrument within the tubular structure and the rotational position of the instrument relative to the tubular structure based on the first and second curvature values. In particular, the position determination unit can be adapted to determine for several segments of the instrument the respective location and rotational position relative to the tubular structure based on the first and second curvature values. Thus, the term "position" preferentially includes the location and the rotational position or orientation of the instrument relative to the tubular structure.

The first curvature values providing unit can be a storing unit in which the first curvature values are stored, wherein the first curvature values providing unit can be adapted to provide the stored first curvature values. However, the first curvature values providing unit can also be a receiving unit for receiving the first curvature values from, for instance, a first curvature values determining unit and for providing the received first curvature values. Moreover, the first curvature values providing unit can also be the first curvature values determining unit itself. Also the second curvature values providing unit can be a storing unit or a receiving unit. Furthermore, the second curvature values providing unit can be a second curvature values determining unit.

The first curvature values are preferentially predetermined. They may have been determined based on a diagnostic image of the tubular structure like a computed tomography image or another diagnostic image. The first curvature values may also be determined in another way. For instance, in a preceding procedure one or several curvature sensors may be moved within the tubular structure such that they are at known first positions within the tubular structure, while the curvatures of the tubular structure are measured by using the one or several sensors.

The tubular structure can be, for instance, a vascular system for blood, a respiratory system, a non-medical pipeline system, a non-medical supply line system, a non-medical tunnel system, et cetera.

In one embodiment the curvature values are one-dimensional. Thus, the position of the instrument within the tubular structure can be determined without using direction-dependent curvature information. In particular, at a respective location two local curvatures can be defined in two different directions like a pitch curvature and a yaw curvature and these two local curvatures can be combined to a one-dimensional curvature value being indicative of the local curvatures at the respective location. For instance, a one-dimensional mean curvature value or a one-dimensional total Gaussian curvature value can be determined. However, the curvature values might also be two-dimensional. For example, the two local curvatures like the pitch curvature and the yaw curvature can be regarded as being the two-dimensional curvature value at the respective location.

In an embodiment the first and second curvature values providing units are adapted to provide one- and two-dimensional first curvature values and one- and two-dimensional second curvature values, wherein the position determination unit is adapted to determine the position of the instrument within the tubular structure based on the one-dimensional first and second curvature values, wherein the position determination unit is further adapted to determine a rotational deviation between the position of the instrument as determined by the position determination unit and the real position of the instrument based on the two-dimensional first and second curvature values. Since the determined position is firstly determined by considering the one-dimensional curvature values only, which are direction independent, i.e. which do not comprise rotational information like torsion or twist information, the location of the instrument within the tubular structure can be correctly determined, but there might be a deviation between the real rotational position of the entire instrument or of a part, i.e. a segment, of the instrument, and the determined rotational position, which might be caused by, for instance, torsions of the instrument, wherein the rotational position relates to a rotation of the instrument around its longitudinal axis. This rotational deviation can be determined by considering the two-dimensional first and second curvature values. In particular, a deviation measure like a root-mean-square deviation measure can be applied to the two-dimensional first and second curvature values for determining the rotational deviation. If the rotational deviation is larger than a deviation threshold, this might be output by an output unit. For instance, a warning might be given to a user or to another device using the determined position.

Preferentially, the position determination unit is further adapted to correct the determined position of the instrument such that the determined rotational deviation is reduced. In particular, the position determination unit is adapted to virtually rotate the entire instrument and/or parts of the instrument in its determined position such that the rotational deviation is reduced, in particular minimized.

The instrument is preferably an interventional instrument to be used inside a patient during a medical procedure. However, the instrument can also be another instrument, especially a non-medical instrument, to be used within the tubular structure. Preferentially the instrument comprises sensors at the several second locations along the instrument, which are adapted to measure the second curvature values being indicative of local curvatures of the instrument at these second locations. These sensors are, for instance, OSS curvature sensors or groups of EM or RFID sensors. For these EM or RFID sensor groups, the relative position with respect to other sensors within the sensor group is sufficient to calculate local curvatures.

Preferentially, the position determination unit is adapted to a) determine for several candidate positions of the instrument within the tubular structure position values, which are indicative of likelihoods that the instrument is arranged at the respective candidate position, based on the first and second curvature values, and b) determine as the position within the tubular structure the candidate position for which the largest position value has been determined. In particular, each candidate position defines which first location matches which second location, wherein the position determination unit is adapted to determine for each candidate position a position value such that it depends on deviations of respective first and second curvature values relative to each other at matching first and second locations. For example, the position determination unit is adapted to determine for each candidate position a position value depending on a sum of squared differences between respective first and second curvature values at matching first and second locations. Determining the position of the instrument within the tubular structure based on these position values can lead to a further improved accuracy of determining this position.

The position determination unit can be adapted to weight the deviations and to determine for each candidate position a position value such that it depends on the weighted deviations. In particular, the position determination unit is adapted to weight the deviations at matching distal locations such that they have a larger influence on the position value than the deviations at other matching locations. Thus, second curvature values at the distal parts of the instrument can be given a higher influence than second curvature values at other second locations along the instrument. Moreover, the weights for second curvature values at certain second locations along the instrument can also be zero. This can be especially useful, if it is known that at one or several second locations the second curvature values might be incorrect. By using this weighting the accuracy of determining the position of the instrument within the tubular structure can be further improved.

In an embodiment the position determination unit is adapted to use temporally varying weights for weighting the deviations. The respective temporally varying weight can depend on at least one member of the following list: a) the second curvature value at the respective second location, b) one or several second curvature values at neighboring second locations, c) the history of the second curvature value at the respective second location, d) the history of the second curvature value at neighboring respective second locations. For instance, initially all weights can have a same predefined value, wherein the weight at a respective second location can be reduced, if the second curvature value at this respective location and one or several second curvature values at one or several neighboring second locations are the same. In particular, the position determination unit can be adapted to, if the second curvature values at a group of neighboring second locations are the same, reduce the weight at one or several central second locations within the group of neighboring second locations. Moreover, in a further example the weight at a respective second location might be reduced, in particular reduced to zero, if the history of second curvature values at this second location indicates fluctuations being smaller than a predefined first threshold or larger than a second threshold being larger than the first threshold. For the history preferentially only a predefined number of previous second curvature values is used such that the history can significantly change over time. If, for instance, after some time the fluctuations indicated by the history are within the first and second thresholds, the respective weight can be increased again.

The tubular structure can be a branching structure such that different possible routes through the tubular structure exist, wherein the position determination unit can be adapted to i) determine, for each possible route, a) for several candidate positions of the instrument within the tubular structure along the respective possible route position values, which are indicative of likelihoods that the instrument is arranged at the respective candidate position, based on the first and second curvature values, and b) the largest position value among these position values, and ii) determine as the position within the tubular structure the candidate position for which the largest overall position value among the largest position values determined for the possible routes has been determined. This allows for an accurate determination of the position of the instrument within the tubular structure with relatively low computational efforts, if the tubular structure comprises several branches.

In an embodiment the position values and the corresponding candidate positions form a function having as input the candidate positions and as output the position values, wherein the position determination device further comprises a quality assessing unit for determining a quality value, which is indicative of the quality of the determination of the position of the instrument within the tubular structure, based on a width of a maximal peak of the function and/or a number of peaks exceeding a threshold. The quality assessing unit can be adapted to determine a first quality value, which is indicative of the precision of the determination of the position of the instrument within the tubular structure, based on the width of the maximal peak of the function. Moreover, the quality assessing unit can be adapted to determine a second quality value, which is indicative of the robustness of the determination of the position of the instrument within the tubular structure, based on the number of peaks exceeding the threshold. This allows a user like a physician to assess the position determination, wherein, for instance, the user can decide whether the position determination is precise and/or robust enough for him/her.

In a preferred embodiment the position determination unit is adapted to a) determine the position values for the candidate positions for different times such that for a respective time a respective set of position values is determined, which correspond to the candidate positions, b) determine a largest connected group of position values, which exceed a threshold, in a space defined by the candidate positions and the time, and c) determine for each time the largest position value within the determined largest connected group of position values, wherein the candidate position, for which this largest position value has been determined, is determined as the position of the instrument within the tubular structure at the respective time. This can lead to a further improved accuracy of determining the position of the instrument within the tubular structure.

Furthermore, taking temporal continuity into account, the search space for subsequent time points can be narrowed down to a neighborhood of the current detected instrument position. This can lead to a reduced calculation time for the calculation of the matching first and second curvature values. For instance, the position determination unit can be adapted to restrict for each time the determination of the largest position value within the determined largest connected group of position values to candidate positions within a region of candidate positions, which includes the candidate position for which the largest position value has been determined for the preceding time. The size of the region might be predefined. The region might be centered on the candidate position for which the largest position value has been determined for the preceding time. In an embodiment the position determination unit is adapted to determine the speed of a movement of the instrument within the tubular structure based on the positions of the instrument within the tubular structure determined for the different times. Thus, not only the position of the instrument, but also its speed relative to the tubular structure can be accurately determined.

In an embodiment the position determination unit is adapted to restrict for each time the determination of the largest position value within the determined largest connected group of position values to candidate positions within a region of candidate positions, which is defined by the preceding candidate position, for which the largest position value has been determined, and the preceding direction of the motion. For instance, the preceding direction of motion can be determined based on the positions of the instrument within the tubular structure determined for different previous times, i.e. based on the candidate positions over previous times, for which the largest position value has been determined at the respective previous time. With this direction of motion from the last time point and a continuity assumption for the instrument motion the region can be centered on the expected instrument position, i.e. the position where the instrument would be located if it is constantly moved with the detected speed of the previous time point.

The tubular structure can comprise a branching point, wherein the position determination unit can be adapted to provide an expected path within the tubular structure, determine a deviation between the first curvature values along the expected path behind the branching point and the second curvature values of the instrument behind the branching point, and determine whether the instrument is moved within the tubular structure along the expected path based on the determined deviation. This allows for a provision of a feedback to a user, while the user moves the instrument within the tubular structure. The expected path can be defined by the user via a graphical user interface based on an image of the tubular structure, or it can be defined automatically or semi-automatically. For instance, a user can indicate the desired final tip position in the image and then the expected path can be automatically determined based on the indicated desired final tip position and the image of the tubular structure.

In a further aspect, an imaging system is presented, wherein the imaging system comprises:
  a position determination device for determining a position of an instrument within a tubular structure as defined in claim 1,
  an image providing unit for providing an image of the tubular structure,
  a visualization generating unit for generating a visualization of the tubular structure based on the provided image and the determined position.

In another aspect, a position determination method for determining a position of an instrument within a tubular structure is presented, wherein the position determination method comprises:

providing first curvature values being indicative of first curvatures of the tubular structure at several first locations along the tubular structure by a first curvature values providing unit, providing second curvature values being indicative of second curvatures of the instrument at several second locations along the instrument by a second curvature values providing unit, and determining the position of the instrument within the tubular structure based on the first and second curvature values by a position determination unit.

In a further aspect, an imaging method is presented, wherein the imaging method comprises:

providing an image of the tubular structure by an image providing unit, determining a position of an instrument within a tubular structure by a position determination device as defined in claim 1, and generating a visualization of the tubular structure based on the provided image and the determined position by a visualization generating unit.

In another aspect, a position determination computer program is presented, wherein the position determination computer program comprises a program code means for causing a position determination device as defined in claim 1 to carry out the position determination method as defined in claim 17, when the computer program is run on the position determination device.

In a further aspect, an imaging computer program is presented, wherein the imaging computer program comprises a program code means for causing an imaging system as defined in claim 1 to carry out the imaging method as defined in claim 18, when the computer program is run on the imaging system.

It shall be understood that the position determination device of claim 1, the imaging system of claim 16, the position determination method of claim 17, the imaging method of claim 18, the position determination computer program of claim 19 and the imaging computer program of claim 20 have similar and/or identical embodiments, in particular, as defined in the dependent claims.

It shall be understood that an embodiment of the present disclosure can also be any combination of the dependent claims or above embodiments with the respective independent claim.

FIG. 1 shows schematically and exemplarily an embodiment of an imaging system 1 comprising a position determination device 5 for determining a position of an instrument 4 within a tubular structure, an image providing unit 10 for providing an image of the tubular structure, and a visualization generating unit 11 for generating a visualization of the tubular structure based on the provided image and the determined position. In this embodiment the tubular structure is a blood vessel structure of a patient 3 lying on a patient table 2. The position determination device 5 comprises a first curvature values providing unit 6 for providing first curvature values being indicative of first curvatures of the tubular structure at several first locations along the tubular structure, wherein in this embodiment the first curvature values providing unit 6 is adapted to determine the first curvature values based on the image provided by the image providing unit 10. In particular, the image providing unit 10 is adapted to provide a three-dimensional image of the tubular structure like a computed tomography image or a magnetic resonance image, which might have been acquired before the instrument 4 has been introduced into the patient 3, i.e. the provided image can be a pre-interventional three-dimensional image. The first curvature values providing unit 6 can be adapted to segment the vessel structure within the provided image and to determine the first curvature values based on the segmentation of the vessel structure in the image.

In this embodiment the instrument 4 is a catheter having OSS sensors at several second locations along the catheter 4. The position determination device 5 comprises a second curvature values providing unit 7 for providing the second curvature values, which are indicative of curvatures of the instrument 4 at the several second locations along the instrument 4, based on optical signals received from the OSS sensors. Thus, in this embodiment the second curvature values providing unit 7 is adapted to determine the second curvature values based on the optical signals received from the OSS sensors arranged along the length of the instrument 4. The first and second curvature values are indicative of curvatures at the respective first and second locations and hence are local curvature values.

The position determination device 5 further comprises a position determination unit 8 for determining the position of the instrument 4 within the tubular structure based on the first and second curvature values. In this embodiment the first and second curvature values are one-dimensional curvature values. In particular, at a respective location two local curvatures can be defined in two different directions and these two local curvatures can be combined to a one-dimensional curvature value being indicative of the local curvatures at the respective location. For instance, a one-dimensional mean curvature value can be determined, for instance, in accordance with following equation:

$$k_m = \tfrac{1}{2} \cdot (k_1 + k_2) \qquad (1)$$

wherein $K_m$ is the one-dimensional mean curvature value, and $k_1$ and $k_2$ are the local curvatures in the two different directions. Also a total (Gaussian) curvature value $K_t$ in accordance with following equation can be calculated:

$$K_t = k_1 k_2 \qquad (2)$$

The variables $k_1$ and $k_2$ can be regarded as being principal curvatures of, for instance, the tubular structure, i.e. the eigenvalues of the shape operator of the tubular structure at the respective location.

The position determination unit 8 is adapted to determine for several candidate positions of the instrument 4 within the tubular structure position values, which are indicative of likelihoods that the instrument 4 is arranged at the respective candidate position, based on the first and second curvature values, and to determine as a position within the tubular structure the candidate position for which the largest position value has been determined. The candidate positions as well as a final position to be determined are relative positions, i.e. positions of the instrument 4 relative to the tubular structure or vice versa. These positions can be defined by the position of the distal tip or of another part of the instrument 4 along a pathway within the tubular structure. If the tubular structure is a branching tubular structure, also the respective pathway within the tubular structure needs to be defined, in order to define the position of the instrument within the tubular structure. Thus, in case of a branching tubular structure the several candidate positions and the position to be finally determined can be defined by the respective pathway and a position of a specified part of the instrument like the distal tip of the instrument along the respective pathway.

Each candidate position defines which first location along the tubular structure matches with which second location along the instrument 4, wherein the position determination unit 8 is adapted to determine for each candidate position a position value depending on deviations of respective first and second curvature values relative to each other at matching first and second locations. Preferentially, the position determination unit 8 is adapted to determine for each candidate position a position value depending on a sum of squared differences between respective first and second curvature values at respective matching first and second locations.

The position determination unit 8 can be adapted to weight the deviations and to determine for each candidate position a position value such that it depends on the weighted deviations. In particular, the position determination unit 8 can be adapted to weight the deviations at matching distal locations such that they have a larger influence on the position values than the deviations at other matching locations.

The determination of the position values based on the candidate positions by using the weighting of the deviations can be regarded as filtering, wherein a filter is applied to the respective candidate position and for each candidate position the respective position value is provided as the filter response.

If the tubular structure is a branching structure such that different possible routes through the tubular structure exist, the position determination unit 8 can be adapted to determine, for each possible route, a) for several candidate positions of the instrument 4 within the tubular structure along the respective possible route position values, which are indicative of likelihoods that the instrument 4 is arranged at the respective candidate position, based on the first and second curvature values, and b) the largest position value among these position values. Moreover, the position determination unit 8 can be adapted to determine as the position within the tubular structure the candidate position for which the largest overall position value among the largest position values determined for the possible routes has been determined. Thus, the filter response, i.e. the position values, can be calculated for all possible routes through the branching tubular structure, wherein an additional max-operation, i.e. selecting the route with maximal filter response, can be used, after the filter response has been determined for all possible routes.

The position values and the corresponding candidate positions can be regarded as forming a function having as input the candidate positions and as output the position values. The position determination device 5 further comprises a quality assessing unit 9 for determining a quality value, which is indicative of the quality of the determination of the position of the instrument 4 within the tubular structure, based on a width of a maximal peak of the function and/or a number of peaks exceeding a threshold. In particular, the quality assessing unit 9 is adapted to determine a first quality value, which is indicative of the precision or accuracy of the determination of the position of the instrument 4 within the tubular structure, based on the width of the maximal peak of the function and to determine a second quality value, which is indicative of the robustness of the determination of the position of the instrument 4 within the tubular structure, based on the number of peaks exceeding the threshold. If the position values are regarded as being a filter response to the candidate positions, the first quality value can also be regarded as being determined based on the width of the maximal filter response peak and the second quality value can be regarded as being determined based on the number of peaks of the filter response exceeding a threshold.

The first quality value can directly be the width of the maximal peak of the function or it can be another value being dependent on the width of the maximal peak of the function. Moreover, the second quality value can directly be the number of peaks exceeding the threshold or it can be another value which depends on the number of peaks exceeding the threshold. The threshold is preferentially predefined and might be modifiable by the user by using an input unit 12 like a keyboard, a computer mouse, a touch pad, etc.

The position determination device 5 can be adapted to determine the position of the instrument 4 within the tubular structure, while the instrument 4 is not moved within the tubular structure, i.e. in a stationary situation, and the position determination device 5 can be adapted to determine the position of the instrument 4 within the tubular structure, while the instrument 4 is moved within the tubular structure, i.e. in a dynamic situation. In particular, the position determination unit 8 of the position determination device 5 can be adapted to determine the position values for the candidate positions for different times such that for a respective time a respective set of position values is determined, which correspond to the candidate positions, wherein a largest connected group of position values, which exceed a threshold, in a space defined by the candidate positions and the time is determined. The position determination unit 8 can be further adapted to determine for each time the largest position value within the determined largest connected group of position values, wherein the candidate position, for which this largest position value has been determined, is determined as a position of the instrument 4 within the tubular structure at the respective time.

The visualization generating unit 11 is adapted to generate the visualization of the tubular structure based on the provided image and the determined position of the instrument within the tubular structure such that the determined position of the instrument is visualized in the provided image or in a further image, which is obtained from the image provided by the image providing unit and which shows desired structures within the patient. The imaging system 1 further comprises an output unit 13 like a display for showing the visualization to a user. Thus, while the instrument 4 is located within the tubular structure of the patient 3, the user can accurately see where the instrument 4 is exactly located within the tubular structure, thereby assisting the user while using the instrument 4 within the patient. For instance, the instrument 4 may have sensing and/or treating capabilities, and the shown visualization can assist the user while performing sensing and/or treating procedures by showing the exact position of, for instance, the tip of instrument 4 relative to the tubular structure on the output unit 13.

Figure 2:
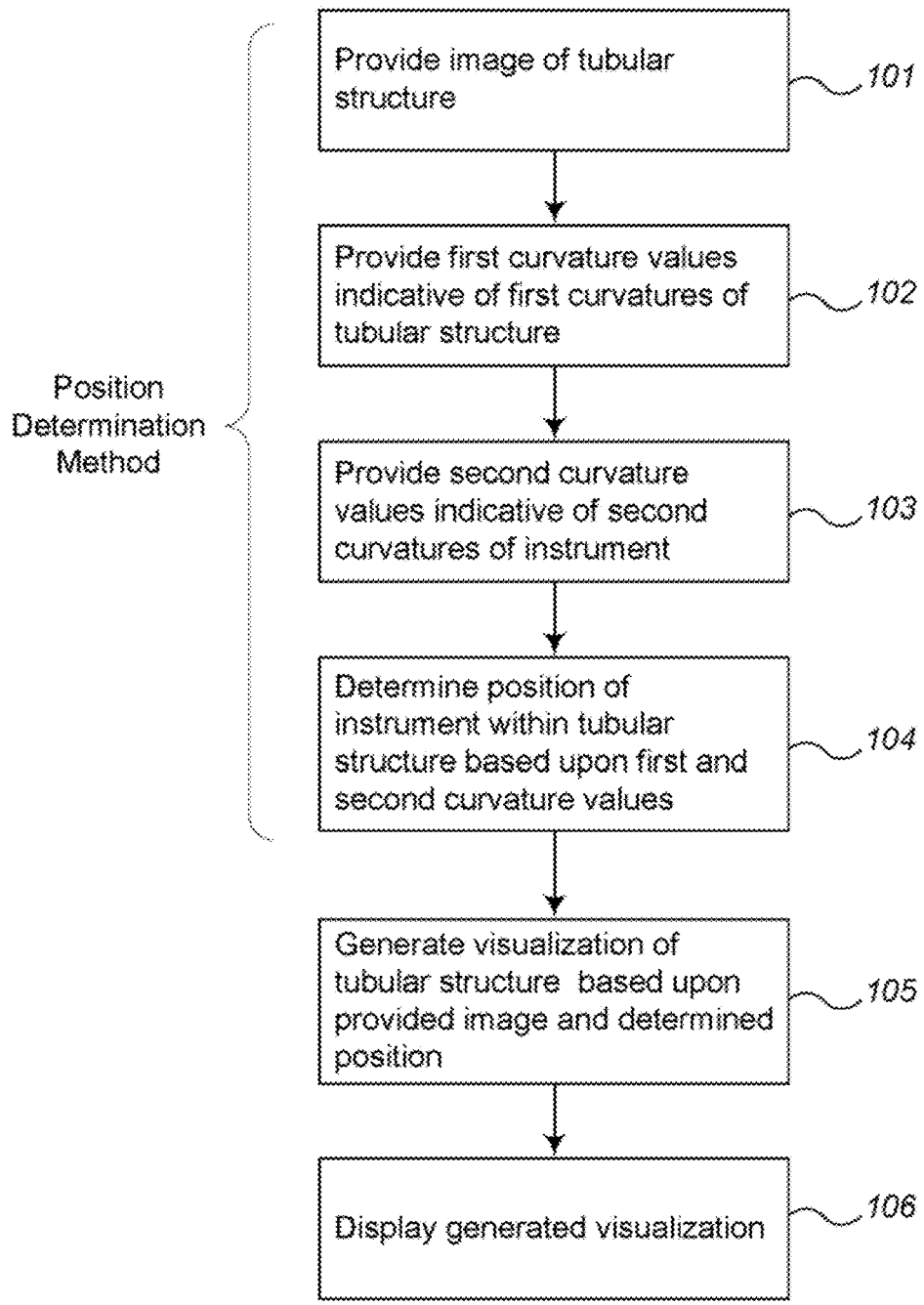
FIG. 2 shows a flowchart exemplarily illustrating an embodiment of an imaging method.

In the following an embodiment of an imaging method will be exemplary described with reference to flowchart shown in FIG. 2.

In step 101 an image of the tubular structure is provided by the image providing unit 10, and in step 102 the first curvature values being indicative of first curvatures of the tubular structure at several first locations along the tubular structure are provided by the first curvature values providing unit 6. These first curvature values can be provided before, during or after the introduction of the instrument 4 into the tubular structure of the patient 3. In step 103, after the instrument 4 has been introduced into the tubular structure of the patient 3, second curvature values being indicative of second curvatures of the instrument 4 at several second locations along the instrument 4 are provided by the second curvature values providing unit 7. In step 104 the position of the instrument 4 within the tubular structure is determined based on the first and second curvature values by the position determination unit 8, and in step 105 a visualization of the tubular structure is generated based on the provided image and the determined position by the visualization generating unit 11, wherein the generated visualization is shown on the output unit 13 in step 106. Steps 102 to 104 can be regarded as being steps of a position determination method for determining a position of an instrument within a tubular structure.

Known tracking systems, which are used in hospitals, provide global position information, i.e. they provide the position of tracked instruments or persons in the Euclidean space. This global information is sensitive to measurement errors due to, for instance, EM field inhomogeneities in case of EM tracking systems or interpolation and integration of curvature information in the case of OSS tracking systems. Moreover, these known tracking systems need a calibration, in order to, for instance, fuse three-dimensional patient images with current patient orientations and hence current positions of instruments within the patient having the respective orientation. This calibration is very sensitive to patient movements and requires a relatively high global positioning accuracy of the tracking system.

By using local curvatures, i.e. the first and second curvature values, for tracking a position of an instrument within a tubular structure these disadvantages can be overcome. For instance, it is not necessary to use the coordinate system of the surrounding, but a patient-specific coordinate system can be used, which is based on the tubular structure within the patient. This coordinate system is invariant to patient movements, i.e. a corresponding calibration is not required. Moreover, global tracking information is not necessary. A direct measurement of local curvatures as carried out by using OSS is sufficient. These local curvatures are compared with predetermined curvatures of the tubular structure, in order to generate a matching between current curvature information and the a priori knowledge about the curvature of the tubular structure, which leads to the current position of the sensors and the instrument relative to the tubular structure. The use of local information leads to smaller measurement inaccuracies in comparison to the use of global tracking techniques and intrinsically prevents the normally dominating error sources like an incorrect movement compensation (heart beat and respiration movement compensation) and global positioning inaccuracies (large measurement field) of global tracking techniques. A relatively small amount of measuring points along the moved structure, i.e. along the instrument, is sufficient, in order to reach a relatively high accuracy.

Figure 3:
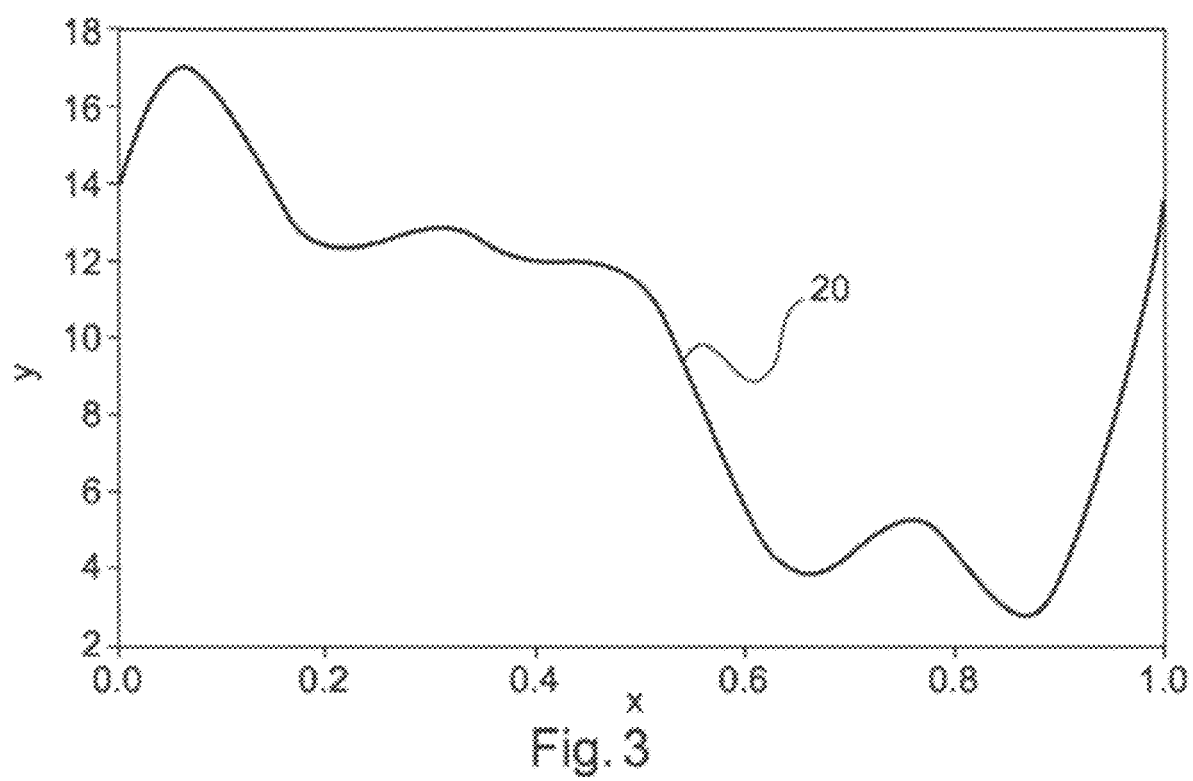
FIG. 3 illustrates exemplarily a shape of a tubular structure.
Figure 4:
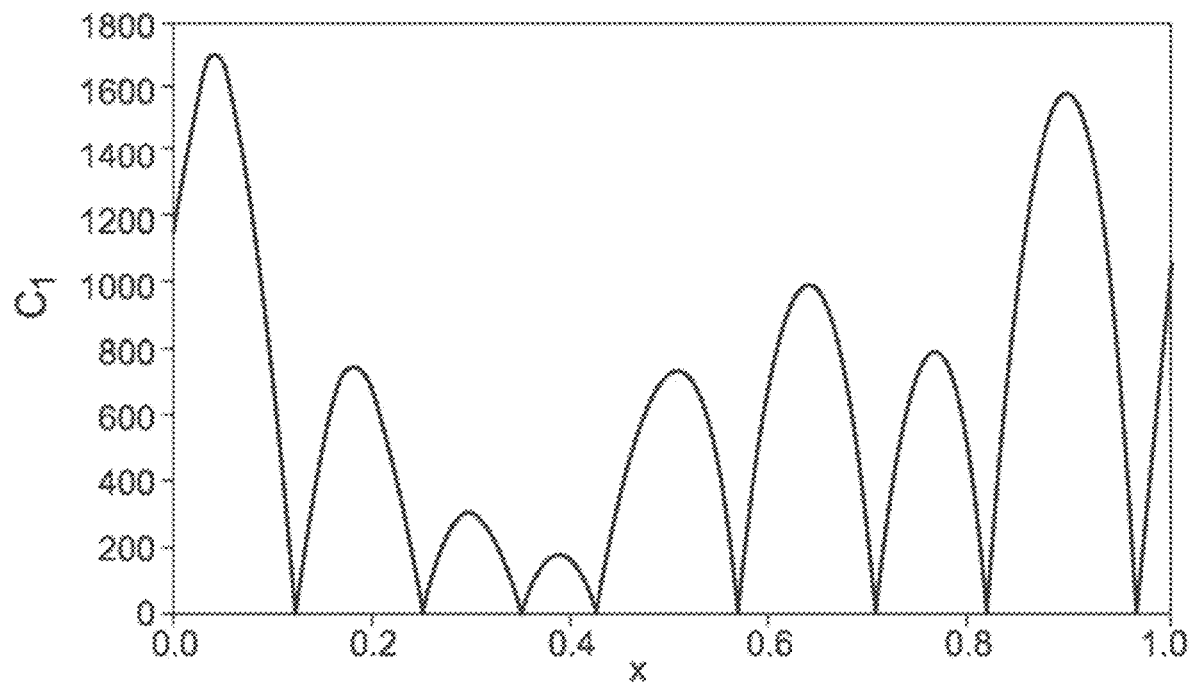
FIG. 4 illustrates exemplarily one-dimensional first curvature values for several first locations along the tubular structure.

Before the position of the instrument within the tubular structure is determined, especially before the instrument is introduced into the tubular structure, preferentially the tubular structure is analyzed based on three-dimensional imaging like computed tomography imaging, magnetic resonance imaging, by biplane angiography, et cetera such that the tubular structure, which might be a branching tubular structure, particularly lengths, shapes and local curvatures of individual tubular segments of the tubular structure, are known beforehand. FIG. 3 illustrates exemplarily a shape 20 of a two-dimensional tubular structure in a two-dimensional spatial coordinate system with axes x and y. Based on this shape 20 local curvatures can be calculated, wherein in this example the local curvatures, i.e. the first curvature values, are one-dimensional. However, in another example the first curvature values can also be two-dimensional with yaw curvature values and pitch curvature values or they can be mean curvatures, which are torsion invariant, in three dimensions. FIG. 4 exemplarily illustrates the one-dimensional first curvature values $c_1$ depending on the first locations x along the tubular structure.

Figure 5:
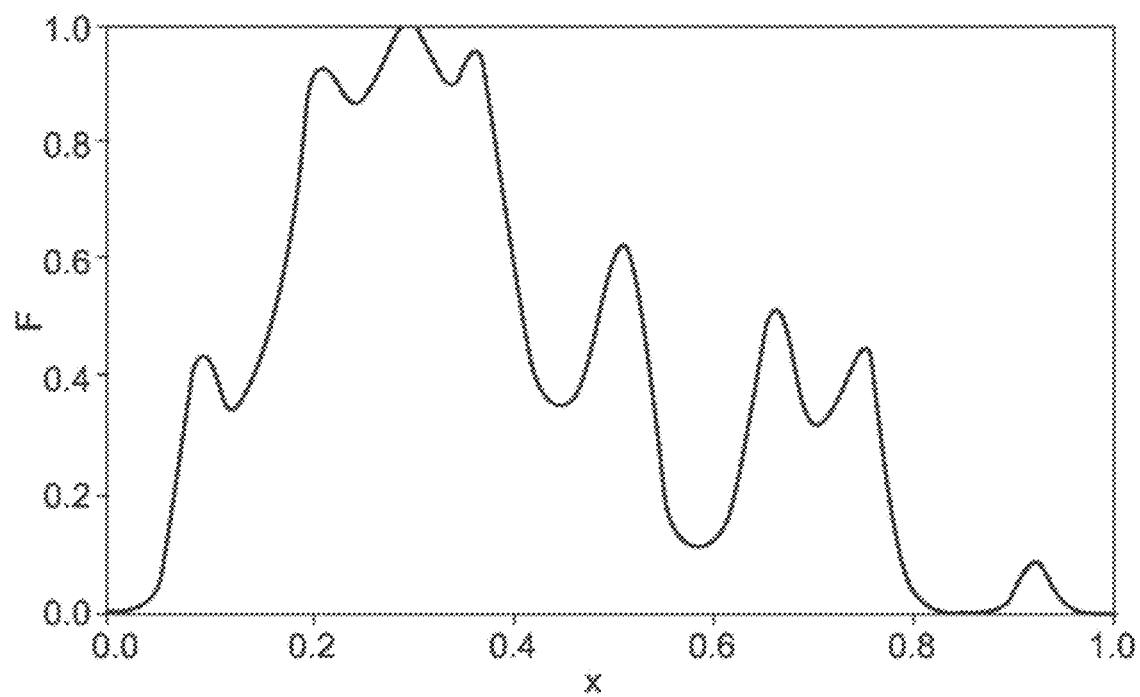
FIG. 5 illustrates exemplarily a filter response for a certain time.

After the instrument has been introduced into the tubular structure, the second curvature values at the second locations along the instrument are measured, wherein these measured local second curvature values are compared to the local first curvature values, in order to determine the position of the instrument within and relative to the tubular structure. In particular, for every possible position of the instrument and hence of the local curvature sensors, i.e. for the several candidate positions, the sensed local second curvature values are compared with the beforehand recorded local first curvature values using a metric for the distance between corresponding beforehand recorded local first curvature values and sensed local second curvature values, thereby generating position values. This generation of the position values can be regarded as applying a filter which uses the metric for the distance between the beforehand recorded local first curvature values and the sensed local second curvature values, wherein the position values can be regarded as being the filter response. FIG. 5 schematically exemplarily illustrates such a filter response F depending on candidate positions x of the instrument relative to the tubular structure.

In FIG. 5 the highest filter response is at the candidate position 0.3. This candidate position can therefore be determined as the position of the instrument within the tubular structure.

Figure 6:
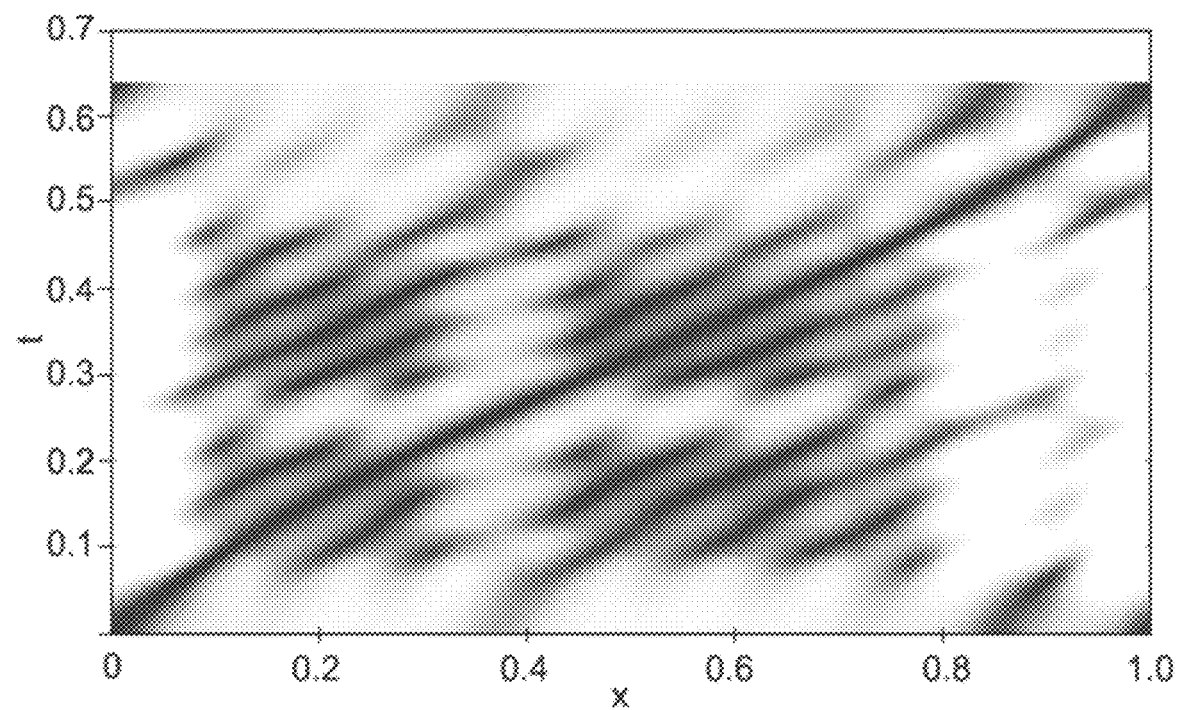
FIG. 6 illustrates exemplarily a filter response over time.
Figure 7:
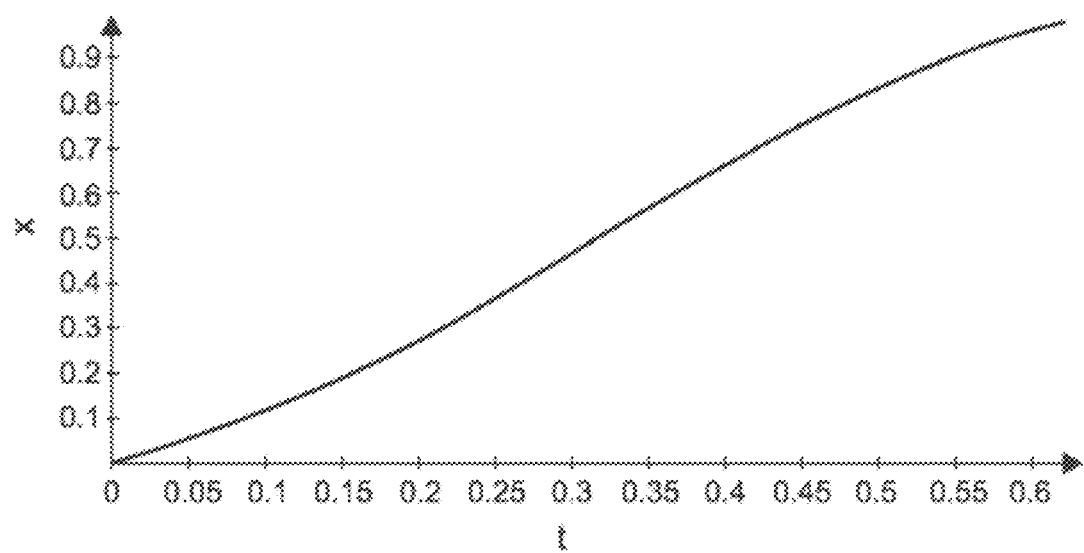
FIG. 7 illustrates exemplarily a determined position of an instrument within the tubular structure over time.
Figure 8:
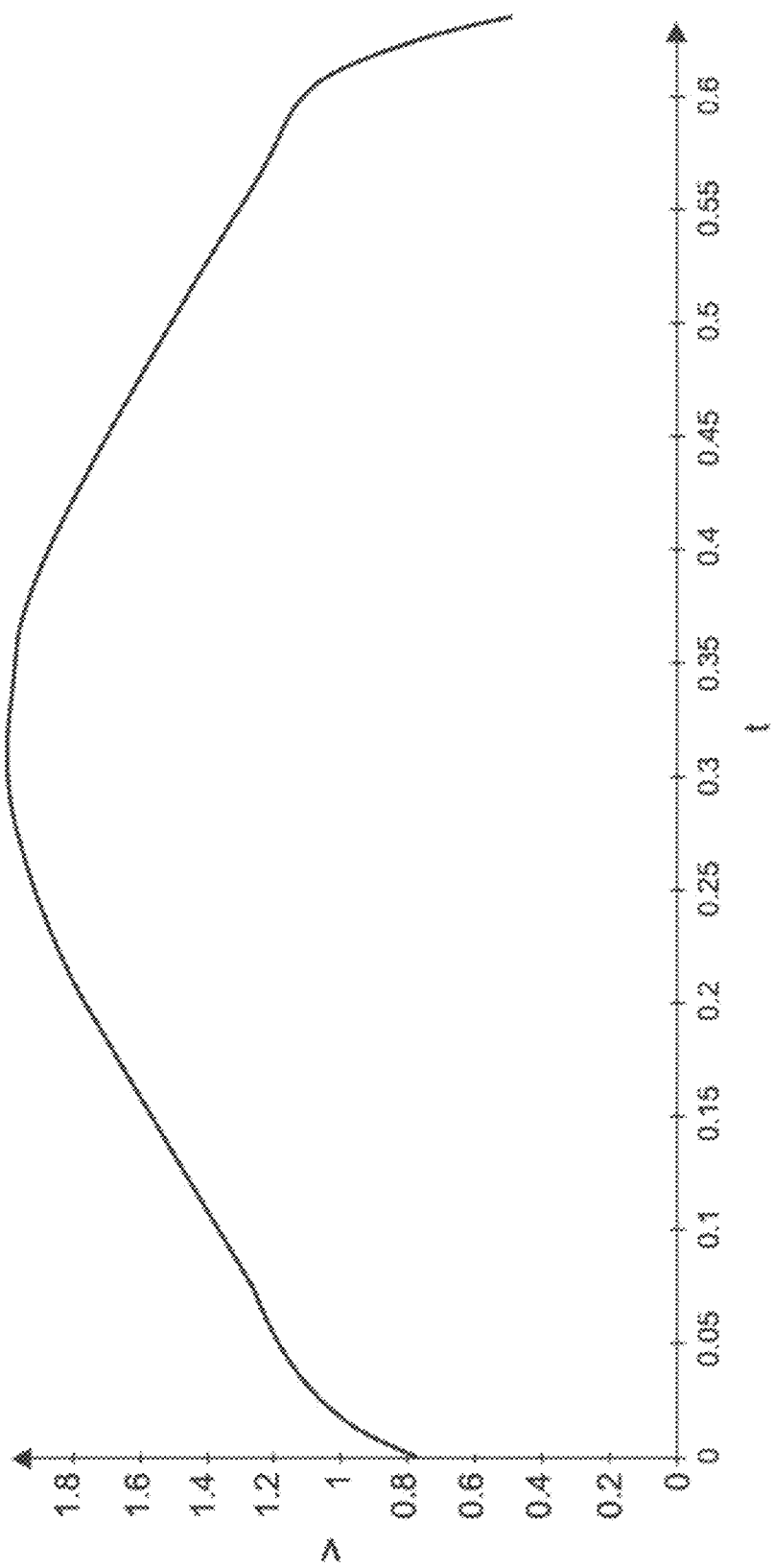
FIG. 8 illustrates exemplarily a speed of a movement of the instrument within the tubular structure.

If the position of the instrument within the tubular structure is determined while the instrument is moved within the tubular structure, the filter response might be plotted as a kind of heat map in an x-t diagram, wherein x is the relative position, i.e. the respective candidate position, within the tubular structure and t is the time. Thus, the local curvature information may be continuously sensed, i.e. the second curvature values may be continuously determined, over time while moving the instrument and hence the sensors inside the tubular structure, wherein the filter response, i.e. the position values, can be calculated for every time step and wherein the filter responses calculated for every time step can be combined in the x-t diagram. FIG. 6 exemplarily illustrates such a diagram, wherein in this example the instrument has been moved within the tubular structure with a speed defined by the function 1+sin(t). For a single time step and for several different candidate positions high filter responses might be calculated. However, for only one candidate position a high filter response should be determined over time, which is visible as a line, which might be curved, in the x-t diagram. The determination of the position of the instrument within the tubular structure over time can therefore be regarded as identifying the "longest line" in the x-t diagram reaching a current time point. This longest line detection can be performed, for instance, by calculating the largest component in the x-t diagram exceeding a prescribed filter response threshold, wherein for a given time point the true position of the instrument within the tubular structure can be determined by detecting the highest peak within this component at the given time point. FIG. 7 exemplarily illustrates the position of the instrument within the tubular structure over time, which has been determined in this way. The position determination device can be adapted to determine the speed of the movement of the instrument within the tubular structure based on this determined position of the instrument within the tubular structure over time. In particular, the slope of the determined time-dependent position can be calculated, in order to determine the speed v. A speed of the instrument within the tubular structure, which has been determined in this way, is exemplarily illustrated in FIG. 8.

The quality assessing unit 9 can be adapted to determine the precision or accuracy of the determined time-dependent position of the instrument within the tubular structure based on the width of the "longest line" detected in the x-t diagram and to determine the reliability of the determined time-dependent position based on the number of "long lines" in the x-t diagram.

The instrument may modify the curvatures of the tubular structure, if the instrument is within the tubular structure and is stiff enough with respect to the stiffness of the tubular structure. This modification of the curvatures of the tubular structure and hence of the first curvature values can reduce the accuracy of the determination of the position of the instrument within the tubular structure. The position determination unit 8 can therefore be adapted to consider this modification when determining the position of the instrument. For instance, the position determination unit 8 can be adapted to use, for instance, a modeling of the sensor-tubular structure interaction and a numerical simulation of the expected modification of the tubular structure, wherein it is assumed that the stiffness of the tubular structure and the stiffness of the instrument are known. However, the position determination unit 8 can also be adapted to user other techniques for considering this modification when determining the position of the instrument like a variational search technique.

The local curvature based intra-tubular navigation provides a moving coordinate system for the tubular structure. This means that the position with respect to the tubular structure is still valid and meaningful after significant movements like breathing movements or heart beat movements. Also all or much of the local curvature information acquired before the procedure is still unchanged after such movements. This is an advantage over alternative approaches that use external reference coordinate systems like EM navigation, fluoroscopy navigation, etc., which require an additional tracking of the tubular structure, in order to achieve precise and meaningful results.

The first and second curvature values providing units 6, 7 can be adapted to provide one- and two-dimensional first curvature values and one- and two-dimensional second curvature values, wherein the position determination unit 8 can be adapted to determine the position of the instrument within the tubular structure based on the one-dimensional first and second curvature values, wherein the position determination unit 8 can be further adapted to determine a rotational deviation between the position of the instrument as determined by the position determination unit 8 and the real position of the instrument based on the two-dimensional first and second curvature values. Since the determined position is determined by considering the one-dimensional curvature values only, which are direction independent, i.e. which do not comprise rotational information like torsion or twist information, the location of the instrument within the tubular structure can be correctly determined, but there might be a deviation between the real rotational position of the entire instrument or of a part, i.e. a segment, of the instrument, and the determined rotational position, which might be caused by, for instance, torsions of the instrument, wherein the rotational position relates to a rotation of the instrument around its longitudinal axis. This rotational deviation can be determined by considering the two-dimensional first and second curvature values. In particular, a deviation measure like a root-mean-square deviation measure can be applied to the two-dimensional first and second curvature values for determining the rotational deviation. If the rotational deviation is larger than a deviation threshold, this might be output by the output unit 13. For instance, a warning might be given to a user via the output unit 13. The position determination unit 8 can be further adapted to correct the determined position of the instrument such that the determined rotational deviation is reduced. In particular, the position determination unit 8 is adapted to virtually rotate the entire instrument and/or parts of the instrument in its determined position such that the rotational deviation is reduced, in particular minimized. Thus, the position of the instrument within the tubular structure might be determined in a two-step approach, wherein in a first step the location of the instrument within the tubular structure is determined by using only the one-dimensional first and second curvature values and wherein in a second step the rotational position of each segment of the instrument is determined such that the rotational deviation is minimized.

The position determination unit can be further adapted to use second curvature values measured along a part of the instrument, which is outside of the tubular structure, together with the position of the end of the tubular structure, which faces this outside, for reconstructing the shape of this part of the instrument outside of the tubular structure. Thus, the matching of the second curvature values of the part of the instrument being within the tubular structure and the first curvature values of the tubular structure can be combined with a shape reconstruction by using the matching approach for the part of the instrument that is inside the tubular structure, for instance, inside a vessel, and a shape reconstruction of the part outside the tubular structure, for instance, within a heart chamber, wherein the reference point for the shape reconstruction is at the end of the tubular structure. In known shape reconstruction systems torsion and instrument rotations are a common error source. If a twist of the instrument is not detected and hence not incorporated in the shape reconstruction, the shape reconstruction continues in a "wrong direction". As explained above, the position determination unit 8 can detect such instrument torsion/twist by comparing the two-dimensional first and second curvature values with each other, in order to determine the above mentioned rotational deviation. Moreover, as also explained above, the rotational deviation can be minimized, particularly eliminated, whereafter a high quality shape reconstruction can be performed by the position determination unit 8.

The provided first curvature values at the first locations along the tubular structure can have been obtained from a previous inspection of the tubular structure such that the position of the instrument obtained from the current intra-tubular examination, provided that the same tubular structure has been reached, can be determined in relation to the positions of the same or another instrument determined during the previous inspection, especially during a previous examination, in a highly reliable fashion.

The instrument with the sensors arranged at the second locations along the instrument can be calibrated by placing the instrument with the sensors in a geometry with known curvatures, in order to compensate for possible manufacturing and/or assembling inaccuracies. Using the local second curvatures sensed by the respective signal sensors directly for the matching represents a one-to-one matching between a sensed and an expected curvature, which allows deriving compensation factors for the local curvature per sensor. These compensation factors can be used during the actual procedure of determining the position of the instrument within the tubular structure together with, for instance, the OSS signals generated for the respective sensors for determining the second curvature values.

The position determination unit may be adapted such that the weights, which are used while calculating the filter response, for the individual sensors, which are used to determine the second curvature values at the second locations, vary over time. However, the weights can also be static. In particular, sensors that tend to give incorrect local second curvature values due to damage and/or deficiency can be "deactivated". Furthermore, this allows giving individual weights to sensors along the instrument to force a higher influence of the distal part, i.e. the part close to the tip of the instrument, on the filter response.

If the local second curvature values are recorded over time, better reconstruction of the three-dimensional shape of the sensed part of the instrument can be obtained. In particular, the position determination unit can be adapted to reconstruct the three-dimensional shape of the sensed part of the instrument, wherein, as soon as a part of the tubular structure has been visited by more than one sensor, the sensor information of all sensors that have passed this part of the tubular structure can be combined, i.e., for instance, averaged, and this combined result can be used for the three-dimensional shape reconstruction.

The position determination unit 8 can be adapted to provide an expected path within the tubular structure, determine a deviation between the first curvature values along the expected path behind a branching point of the tubular structure and the second curvature values of the instrument behind the branching point, and determine whether the instrument is moved within the tubular structure along the expected path based on the determined deviation. Thus, while inserting the instrument into the tubular structure, the position determination unit 8 can be adapted to determine whether the tip of the instrument is moved in the right direction at a branching point. For instance, a deviation measure like a root-mean-square deviation can be applied to the first curvature values along the expected path behind the branching point and to the second curvature values of the instrument behind the branching point. If this leads to a deviation result being larger than a threshold, which might be predefined, it can be indicated to the user that the tip has likely be moved in a wrong direction. The threshold can also be dependent on a deviation of the first and second curvature values before the branching point. For instance, the threshold can be defined as an allowed absolute or relative difference between the deviations before and behind the branching point.

The visualization generating unit can be adapted to generate the visualization such that a prior two- or three-dimensional image like an intravascular ultrasound (IVUS), CT or MR image provided by the image providing unit is displayed around the calculated instrument tip position or along the matched second curvature positions, in order to yield a virtual endoscopy or surround view. This might be beneficial for procedures in which complex information is available from prior two- or three-dimensional imaging scans.

The position determination device can be adapted to additionally use tracking, navigation, and positioning information from further devices for tracking the instrument within the tubular structure. For instance, if for measuring the second curvature values at the several second locations along the instrument OSS sensors are used, a further device may be a tracking device to track the position of the instrument within the tubular structure by using an EM tracking technique or fluoroscopy. For example, an x-ray C-arm could be used for acquiring one or several validation images, which can be used by the position determination unit of the position determination device for increasing the level of confidence that a specific position within the tubular structure has been reached by the instrument. In a further example, position information from a robotic steering unit for steering the instrument can be used by the position determination unit of the position determination device for increasing the level of confidence that a specific position within the tubular structure has been reached by the instrument.

Thus, the position determination unit can be adapted to use the first and second curvature values for determining the position of the instrument within the tubular structure and to combine this positional information with other tracking and/or navigation and/or position information, in order to determine an optionally adapted position of the instrument. This might be done by weighting the influence from various sources based on the confidence of the provided position information. Thus, for each information source a degree of confidence might be provided and the position determination unit can be adapted to weight the information sources depending on the provided degrees of confidence, when combining these information sources for adapting the determined position of the instrument. For example, positional information obtained by clearly detecting the instrument in a fluoroscopy image can have a relatively high degree of confidence; in particular the degree of confidence can be higher than the degree of confidence of possibly rough navigation information from a robotic steering unit.

The position determination unit can also be adapted to combine EM tracking information being indicative of the position of the instrument tip within the tubular structure with OSS, which can be used for determining the second curvature values at the second locations along the instrument, in order to provide complementary information. For example, if the EM tracking information indicates that the instrument tip is moving with respect to an EM coordinate system defined by the EM tracking device, but if the curvature information indicates that the instrument is not moving with respect to the tubular structure, the position determination unit can determine that the movement is due to patient motion like breathing motion or heart beat motion and not due to instrument displacement within the tubular structure. Thus, the position determination unit can be adapted to provide complementary information like whether there is patient motion and not motion of the instrument with respect to the tubular structure based on the curvature information and based on the further tracking information. In this case the position determination unit or another unit can be further adapted to determine the patient motion, for instance, breathing motion and/or heartbeat motion, based on the further tracking information.

In an embodiment the instrument, especially the tip of the instrument, comprises an imaging unit like an intravascular ultrasound (IVUS) unit. The visualization generating unit can be adapted to construct a two-dimensional image based on one-dimensional rotational images acquired by the imaging unit, while the instrument is moved within the tubular structure, and based on the respective position of the instrument within the tubular structure, wherein the position also includes the rotational position of the instrument within the tubular structure. Thus, at each point in time the position determination device determines the position along a pathway through the tubular structure and the rotational position of the instrument such that at each point in time the spatial orientation of the imaging unit with respect to the tubular structure is known. This information is used by the visualization generating unit for reconstructing a two-dimensional image based on the one-dimensional rotational images acquired by the imaging unit. It is therefore possible to generate the two-dimensional image during, for instance, a retraction movement of the instrument within the tubular structure, without the need of constant retraction speed or the need of avoiding rotations, as it is usually the case with retraction-based two-dimensional imaging reconstructions. In addition, since in this embodiment the position determination device determines the position of the instrument along a pathway within the tubular structure and the rotational position of the instrument with respect to the tubular structure, the position determination device can also provide information about the current orientation of the instrument, in particular of the instrument tip, with respect to neighboring vessel parts, if the tubular structure is a vessel structure including the neighboring vessel parts. In this situation the two-dimensional image reconstruction can also be based on non-parallel coordinates along the curved centerline of the tubular structure and thus can become more accurate and compensate for the rotational motion of the instrument tip. In another embodiment the visualization generating unit can be adapted to construct a three-dimensional image based on two-dimensional images acquired by the imaging unit, while the instrument is moved within the tubular structure, and based on the respective position of the instrument within the tubular structure, wherein the position also includes the rotational position of the instrument within the tubular structure.

The tracking of the position of the instrument within the tubular structure including the rotational position of the instrument within the tubular structure based on the curvature information can be used to position the instrument within the tubular structure as desired in a reproducible way, wherein not only the position along the respective pathway within the tubular structure, i.e. the location, but also the rotational position of the instrument with respect to the tubular structure can be set in a reproducible way. For instance, if a desired position of the instrument within the tubular structure is given, which might be the same position as used in a previous intervention, firstly the instrument can be arranged within the tubular structure such that its location corresponds to the desired location by using only one-dimensional curvature values for the calculation of the current position of the instrument. Then the instrument can be virtually rotated such that deviations between two-dimensional second curvature values of the instrument and two-dimensional curvature values indicating the desired rotational position are minimized. The two-dimensional curvature values indicating the desired rotational position can be the two-dimensional second curvature values of the instrument which were present while the instrument was in the desired position in a previous intervention to be reproduced. The clinically relevant problem of achieving reproducible images acquired by an imaging unit of the instrument, especially of achieving reproducible IVUS examinations, can therefore be solved without any further navigation aid or external imaging control. The position determination unit, the visualization generating unit or another unit of the imaging system can even be adapted to warn the user, who might be a clinician and who performs the intervention that a wrong vessel branch has been reached, if the robustness and precision of the matching of first and second curvature values along the expected path of the instrument is too small.

By using a local patient-specific coordinate system the determination of the position of the instrument within the tubular structure can be substantially independent of the global position of possibly tracked devices and/or persons. Patient movements, movements of equipment during an intervention, repositioning and transport of a patient, et cetera, do therefore not adversely affect the determination of the position of the instrument within the tubular structure. Moreover, tracking techniques can be used which provide an insufficient global accuracy, but which provide a sufficient local relative accuracy, i.e. the global, GPS-like localization is not relevant as long as the local information, distance and angle, of, for instance, neighboring position sensors can be accurately determined for a local curvature calculation. In particular, a group of at least three position sensors, which is arranged at a certain location, can be used for determining a curvature value for this location only based on relative position information, i.e. based on the positions of the positions sensors of the group relative to each other. In case of OSS sensors, only one OSS per location along the instrument can be enough for determining a curvature value for the respective location.

Since the position determination is based on measuring local curvatures along the instrument, an accumulation of errors due to an integration of the curvature measurements along the instrument can be avoided. Moreover, if the curvatures are measured in a temporally continuous way, the position determination can be more stabilized and quality measures being indicative of the quality of determining the position can be derived. Moreover, due to the matching of the first and second curvature values measurement errors and deformations of the tubular structure do not necessarily lead to positioning errors, because they can be compensated by a "best fit" approach.

Other variations to the disclosed embodiments can be understood and effected by those skilled in the art in practicing the claimed disclosure, from a study of the drawings, the disclosure, and the appended claims.

In the claims, the word "comprising" does not exclude other elements or steps, and the indefinite article "a" or "an" does not exclude a plurality.

A single unit or device may fulfill the functions of several items recited in the claims. The mere fact that certain measures are recited in mutually different dependent claims does not indicate that a combination of these measures cannot be used to advantage.

Operations like the determination of the position of the instrument within the tubular structure, the determination of quality values, et cetera performed by one or several units or devices can be performed by any other number of units or devices. These operations and/or the control of the imaging system in accordance with the imaging method and/or the control of the position determination device in accordance with the position determination method can be implemented as program code means of a computer program and/or as dedicated hardware.

A computer program may be stored/distributed on a suitable medium, such as an optical storage medium or a solid-state medium, supplied together with or as part of other hardware, but may also be distributed in other forms, such as via the Internet or other wired or wireless telecommunication systems.

Any reference signs in the claims should not be construed as limiting the scope.

All of the above U.S. patents, U.S. patent application publications, U.S. patent applications, foreign patents, foreign patent applications and non-patent publications referred to in this specification and/or listed in the Application Data Sheet, including but not limited to International Patent Application No. PCT/EP2017/076101, filed Oct. 12, 2017; Germany Patent Application No. 102016119579.0, filed Oct. 13, 2016, are incorporated herein by reference, in their entireties.

From the foregoing it will be appreciated that, although specific embodiments have been described herein for purposes of illustration, various modifications may be made without deviating from the spirit and scope of the invention. Also, the methods and systems discussed herein are applicable to differing protocols, communication media (optical, wireless, cable, etc.) and devices (such as wireless handsets, electronic organizers, personal digital assistants, portable email machines, game machines, pagers, navigation devices such as GPS receivers, etc.).

The invention claimed is:

1. A position determination computing device for determining a position of an instrument within a tubular structure, the position determination device comprising:
   a first curvature values providing unit configured to provide first curvature values being indicative of first curvatures of the tubular structure at several first locations along the tubular structure;
   a second curvature values providing unit configured to provide second curvature values being indicative of second curvatures of the instrument at several second locations along the instrument; and
   a position determination unit configured to provide the position of the instrument within the tubular structure based on the first and second curvature values, wherein the position determination unit is configured to a) determine, for several candidate positions of the instrument within the tubular structure position, values that are indicative of likelihoods that the instrument is arranged at the respective candidate position, based on the first and second curvature values; and b) determine, as the position within the tubular structure, the candidate position for which the largest position value has been determined.

2. The position determination computing device of claim 1, wherein each candidate position defines which first location matches which second location, wherein the position determination unit is configured to determine for each candidate position a position value based on deviations of respective first and second curvature values relative to each other at matching first and second locations.

3. The position determination computing device of claim 2, wherein the position determination unit is configured to weight the deviations and to determine for each candidate position a position value such that it depends on the weighted deviations.

4. The position determination computing device of claim 3, wherein the position determination unit is configured to use temporally varying weights for weighting the deviations.

5. The position determination computing device of claim 1, wherein the tubular structure is a branching structure such that different possible routes through the tubular structure exist, wherein the position determination unit is further configured to:
   determine, for each possible route, a) for several candidate positions of the instrument within the tubular structure along the respective possible route position values, which are indicative of likelihoods that the instrument is arranged at the respective candidate position, based on the first and second curvature values, and b) the largest position value among these position values; and
   determine as the position within the tubular structure the candidate position for which the largest overall position value among the largest position values determined for the possible routes has been determined.

6. The position determination computing device of claim 1, wherein the position values and the corresponding candidate positions form a function having as input the candidate positions and as output the position values, wherein the position determination device further comprises a quality assessing unit for determining a quality value, which is indicative of the quality of the of the determination of the position of the instrument within the tubular structure, based on a width of a maximal peak of the function and/or a number of peaks exceeding a threshold.

7. The position determination computing device of claim 6, wherein the quality assessing unit is configured to determine a first quality value, which is indicative of the precision of the determination of the position of the instrument within the tubular structure, based on the width of the maximal peak of the function.

8. The position determination computing device of claim 6, wherein the quality assessing unit is configured to determine a second quality value, which is indicative of the robustness of the determination of the position of the instrument within the tubular structure, based on the number of peaks exceeding the threshold.

9. The position determination computing device of claim 1, wherein the position determination unit is configured to:
   determine the position values for the candidate positions for different times such that for a respective time a respective set of position values is determined that correspond to the candidate positions;
   determine a largest connected group of position values, which exceed a threshold, in a space defined by the candidate positions and the time; and
   determine for each time the largest position value within the determined largest connected group of position values, wherein the candidate position, for which this largest position value has been determined, is determined as the position of the instrument within the tubular structure at the respective time.

10. The position determination computing device of claim 9, wherein the position determination unit is configured to determine the speed of a movement of the instrument within the tubular structure based on the positions of the instrument within the tubular structure determined for the different times.

11. The position determination computing device of claim 1, wherein the provided first and second curvature values are one-dimensional values.

12. The position determination computing device of claim 1, wherein the first and second curvature values providing units are configured to provide one- and two-dimensional first curvature values and one- and two-dimensional second curvature values, wherein the position determination unit is configured to determine the position of the instrument within the tubular structure based on the one-dimensional first and second curvature values, wherein the position determination unit is further configured to determine a rotational deviation between the position of the instrument as determined by the position determination unit and the real position of the instrument based on the two-dimensional first and second curvature values.

13. The position determination computing device of claim 12, wherein the position determination unit is further configured to correct the determined position of the instrument such that the rotational deviation is reduced.

14. The position determination computing device of claim 1, wherein the tubular structure comprises a branching point, wherein the position determination unit is configured to:
provide an expected path within the tubular structure;
determine a deviation between the first curvature values along the expected path behind the branching point and the second curvature values of the instrument behind the branching point; and
determine whether the instrument is moved within the tubular structure along the expected path based on the determined deviation.

15. An imaging computing system comprising:
a position determination device configured to determine a position of an instrument within a tubular structure as defined in claim 1;
an image providing unit configured to provide an image of the tubular structure; and
a visualization generating unit configured to generate a visualization of the tubular structure based on the provided image and the determined position.

16. An imaging method in a computing system comprising:
providing an image of a tubular structure by an image providing unit;
determining a position of an instrument within a tubular structure by a position determination device as defined in claim 1; and
generating a visualization of the tubular structure based on the provided image and the determined position by a visualization generating unit.

17. A non-transitory computer-readable storage medium comprising program code instructions that, when executed on a computer processor, cause an imaging system perform an imaging method comprising:
providing an image of a tubular structure by an image providing unit;
determining a position of an instrument within a tubular structure by a position determination device as defined in claim 1; and
generating a visualization of the tubular structure based on the provided image and the determined position by a visualization generating unit.

18. A computer-implemented position determination method for determining a position of an instrument within a tubular structure, the position determination method comprising:
providing first curvature values being indicative of first curvatures of the tubular structure at several first locations along the tubular structure by a first curvature values providing unit;
providing second curvature values being indicative of second curvatures of the instrument at several second locations along the instrument by a second curvature values providing unit; and
determining the position of the instrument within the tubular structure based on the first and second curvature values by a position determination unit, wherein the position determination unit a) determines, for several candidate positions of the instrument within the tubular structure position, values that are indicative of likelihoods that the instrument is arranged at the respective candidate position, based on the first and second curvature values; and b) determines, as the position within the tubular structure, the candidate position for which the largest position value has been determined.

19. A non-transitory computer-readable storage medium comprising program code instructions that, when executed on a computer processor, cause a position determination device to perform a position determination method comprising:
providing first curvature values being indicative of first curvatures of the tubular structure at several first locations along the tubular structure by a first curvature values providing unit;
providing second curvature values being indicative of second curvatures of the instrument at several second locations along the instrument by a second curvature values providing unit; and
determining the position of the instrument within the tubular structure based on the first and second curvature values by a position determination unit, wherein the position determination unit a) determines, for several candidate positions of the instrument within the tubular structure position, values that are indicative of likelihoods that the instrument is arranged at the respective candidate position, based on the first and second curvature values; and b) determines, as the position within the tubular structure, the candidate position for which the largest position value has been determined.

* * * * *

UNITED STATES PATENT AND TRADEMARK OFFICE
CERTIFICATE OF CORRECTION

PATENT NO. : 10,925,679 B2  
APPLICATION NO. : 16/341810  
DATED : February 23, 2021  
INVENTOR(S) : Horst Hahn et al.

Page 1 of 1

It is certified that error appears in the above-identified patent and that said Letters Patent is hereby corrected as shown below:

In the Claims

In Column 20, Line 22 (Claim 1), the second occurrence of "of the" should be removed.

In Column 21, Line 45 (Claim 17), between "system" and "perform" insert --to--.

Signed and Sealed this  
Twentieth Day of April, 2021

Drew Hirshfeld  
*Performing the Functions and Duties of the*  
*Under Secretary of Commerce for Intellectual Property and*  
*Director of the United States Patent and Trademark Office*